(12) United States Patent
Matheny

(10) Patent No.: US 9,283,302 B2
(45) Date of Patent: *Mar. 15, 2016

(54) EXTRACELLULAR MATRIX ENCASEMENT STRUCTURES AND METHODS

(71) Applicant: CORMATRIX CARDIOVASCULAR, INC., Roswell, GA (US)

(72) Inventor: Robert G Matheny, Norcross, GA (US)

(73) Assignee: CORMATRIX CARDIOVASCULAR, INC., Roswell, GA (US)

(*) Notice: Subject to any disclaimer, the term of this patent is extended or adjusted under 35 U.S.C. 154(b) by 118 days.

This patent is subject to a terminal disclaimer.

(21) Appl. No.: 13/896,424

(22) Filed: May 17, 2013

(65) Prior Publication Data

US 2014/0343673 A1    Nov. 20, 2014

Related U.S. Application Data

(63) Continuation-in-part of application No. 13/573,566, filed on Sep. 24, 2012.

(51) Int. Cl.

| | | |
|---|---|---|
| A61K 35/12 | (2015.01) |
| A61K 9/16 | (2006.01) |
| A61F 13/00 | (2006.01) |
| A61L 33/00 | (2006.01) |
| A61N 1/362 | (2006.01) |
| A61L 27/36 | (2006.01) |
| A61L 31/00 | (2006.01) |
| A61F 2/02 | (2006.01) |
| A61L 27/54 | (2006.01) |
| A61K 35/38 | (2015.01) |
| A61K 35/22 | (2015.01) |
| A61F 2/24 | (2006.01) |
| A61K 38/00 | (2006.01) |

(52) U.S. Cl.
CPC ............ *A61L 27/3629* (2013.01); *A61F 2/02* (2013.01); *A61L 27/3604* (2013.01); *A61L 27/3633* (2013.01); *A61L 27/54* (2013.01); *A61L 31/005* (2013.01); *A61F 2/24* (2013.01); *A61K 35/12* (2013.01); *A61K 35/22* (2013.01); *A61K 35/38* (2013.01); *A61K 38/005* (2013.01); *A61L 27/3679* (2013.01); *A61L 2300/414* (2013.01); *A61L 2300/64* (2013.01); *A61L 2430/20* (2013.01)

(58) Field of Classification Search
CPC ............ A61F 2/02; A61F 2/24; A61K 35/12; A61K 35/22; A61K 35/38; A61K 38/005; A61L 27/3633; A61L 27/3679
USPC ............ 424/422, 490, 572; 427/2.24; 600/16
See application file for complete search history.

(56) References Cited

U.S. PATENT DOCUMENTS

| | | |
|---|---|---|
| 2008/0125851 A1* | 5/2008 | Kilpatrick et al. |
| 2008/0175980 A1* | 7/2008 | Sun |
| 2009/0163951 A1* | 6/2009 | Simmons et al. |
| 2009/0204228 A1* | 8/2009 | Hiles |
| 2010/0262221 A1* | 10/2010 | Schafer et al. |
| 2012/0156255 A1* | 6/2012 | Singh et al. |

OTHER PUBLICATIONS

Shandling, et al., Dacron-Woven Pacemaker Pouch—Influence on Long-term Pacemaker Mobility, Chest, vol. 99, pp. 660-662 (1991).
Ty RX Pharma Aigis Rx Antibacterial Envelope Informational Brochure (2012).

* cited by examiner

*Primary Examiner* — Shin Lin Chen
(74) *Attorney, Agent, or Firm* — Francis Law Group

(57) ABSTRACT

A remodelable encasement structure comprising a pouch formed from at least one sheet of bioremodelable material, the pouch including an internal region and at least one lead conduit, the internal region being configured to receive a device therein, the lead conduit being configures to receive at least one device lead therein, the bioremodelable material comprising an extracellular matrix (ECM) composition that includes an ECM component derived from a mammalian source.

4 Claims, 4 Drawing Sheets

EXTRACELLULAR MATRIX ENCASEMENT STRUCTURES AND METHODS

CROSS-REFERENCES TO RELATED APPLICATIONS

This application is a continuation-in-part of U.S. application Ser. No. 13/573,566, filed on Sep. 24, 2012, which is a continuation-in-part of U.S. application Ser. No. 13/328,287, filed on Dec. 16, 2011.

FIELD OF THE INVENTION

The present invention relates to implantable devices. More particularly, the present invention relates to implantable structures and devices; particularly, medical devices, encased in extracellular matrix (ECM) based pouches and/or include ECM based coatings that effectuate modulated healing of damaged tissue and regeneration of new tissue structures with site-specific structural and functional properties.

BACKGROUND OF THE INVENTION

As is well known in the art, treatment of various medical conditions commonly involves implantation of medical devices and/or insertion of medical instruments into a body. Illustrative is the implantation or deployment of heart valves to regulate the flow of blood through cardiovascular vessels, and pacemakers to control abnormal heart rhythms.

Implantable medical devices; particularly, cardiovascular implants, have unique blood biocompatibility requirements to ensure that the device is not rejected (as in the case of natural tissue materials for heart valves and grafts for heart transplants) or that adverse thrombogenic (clotting) or hemodynamic (blood flow) responses are avoided.

Several cardiovascular implants, such as heart valves, are formed from natural tissue. Illustrative are the heart valves disclosed in U.S. Pat. Nos. 6,719,788 and 5,480,424 to Cox. The disclosed bioprostheses can, however, be affected by gradual calcification, which can, and in many instances will, lead to the eventual stiffening and tearing of the implant.

Many non-bioprosthetic implants are, however, fabricated from various metals and polymeric materials, and other exotic materials, such as pyrolytic carbon-coated graphite.

For example, pacemakers, defibrillators, leads, and other similar cardiovascular implants are often fabricated from Ni—Co—Cr alloy, Co—Cr—Mo alloy, titanium, and Ti-6Al-4V alloy, stainless steel, and various biocompatible polymeric materials. Artificial heart valves are often fabricated from various combinations of nylon, silicone, titanium, Teflon™, polyacetal, graphite and pyrolytic carbon.

Artificial hearts and ventricular assist devices are often fabricated from various combinations of stainless steel, cobalt alloy, titanium, Ti-6Al-4V alloy, carbon fiber reinforced composites, polyurethanes, Biolon™, Hemothane™, Dacron™, polysulfone, and other thermoplastics.

Finally, catheters and guide wires are often fabricated from Co—Ni or stainless steel wire. In many instances, the wire is encased in a polymeric material.

As is well known in the art, several major problems are often encountered when a medical device (or other device, e.g., tracking apparatus) fabricated from one of the aforementioned materials is implanted in the body. A major problem that is often encountered after implantation of such a device in the body is inflammation of surrounding tissue.

Another major problem is the high incidence of infection.

A further problem that is often encountered after implantation of the medical device in the body is the formation of blood clots (thrombogenesis).

One additional problem that is also often encountered is the degradation, e.g., corrosion, of medical device leads and, thereby, premature failure of the device after implantation in the body.

Most medical devices are designed to be implanted in the body for an extended period of time. However, when a harsh biological response (or premature failure of the device) is encountered after implantation, it is often necessary to remove the device through a secondary surgical procedure, which can, and in many instances will, result in undesirable pain and discomfort to the patient, and possibly additional trauma to the adjacent tissue. In addition to the pain and discomfort, the patient must be subjected to an additional time consuming and complicated surgical procedure with the attendant risks of surgery.

There is thus a need to provide medical devices that are configured for implantation in the body, and substantially reduce or eliminate the harsh biological responses associated with conventional implanted medical devices, including inflammation, infection and thrombogenesis.

It is therefore an object of the present invention to provide encasement structures that are configured to encase a medical device therein and that substantially reduce or eliminate the harsh biological responses associated with conventional implanted medical devices, including inflammation, infection and thrombogenesis, when implanted in the body.

It is another object of the present invention to provide ECM encasement structures that are configured to encase a medical device therein, and effectively improve biological functions and/or promote modulated healing of adjacent tissue and the growth of new tissue when implanted in the body.

It is another object of the present invention to provide ECM encasement structures that are configured to encase a medical device therein and administer one or more pharmacological or therapeutic agents when implanted in the body.

It is yet another object of the present invention to provide medical devices that are configured for insertion or implantation in the body and exhibit enhanced biocompatibility and hemocompatibility when inserted or implanted therein.

SUMMARY OF THE INVENTION

The present invention is directed to extracellular matrix (ECM) encasement structures and compositions for encasing devices; particularly, medical devices.

In some embodiments of the invention, the ECM encasement structures comprise a pocket or pouch that is configured to receive a device therein. In some embodiments, the device comprises a medical device.

According to the invention, the medical device can comprise, without limitation, a pacemaker, defibrillator, synthetic heart valve, ventricular assist device, artificial heart, physiological sensor, catheter, and associated components, e.g., the electrical leads and lines associated therewith.

In a preferred embodiment, the ECM encasement structures are configured to encase an entire medical device.

In some embodiments, the ECM encasement structures are also configured to encase at least a portion of the medical device electrical leads.

In some embodiments of the invention, the ECM encasement structures include lead conduits that are configured to encase the medical device leads.

In a preferred embodiment, the ECM encasement structures comprise (or is constructed of) an ECM composition that includes at least one ECM material.

In other embodiments of the invention, there are provided medical devices that are configured for insertion or implantation in the body and include at least one coating of an ECM composition; the ECM composition similarly including at least one ECM material.

In a preferred embodiment, the ECM material referenced above comprises mammalian extracellular matrix tissue selected from the group comprising small intestine submucosa (SIS), urinary bladder submucosa (UBS), stomach submucosa (SS), central nervous system tissue, epithelium of mesodermal origin, i.e. mesothelial tissue, dermal extracellular matrix, subcutaneous extracellular matrix, gastrointestinal extracellular matrix, i.e. large and small intestines, tissue surrounding growing bone, placental extracellular matrix, ornamentum extracellular matrix, cardiac extracellular matrix, e.g., pericardium and/or myocardium, kidney extracellular matrix, pancreas extracellular matrix, lung extracellular matrix, and combinations thereof.

In some embodiments of the invention, the ECM material and, hence ECM encasement structures formed therefrom include at least one additional biologically active agent or composition, i.e. an agent that induces or modulates a physiological or biological process, or cellular activity, e.g., induces proliferation, and/or growth and/or regeneration of tissue.

In some embodiments of the invention, the biologically active agent comprises a growth factor.

In some embodiments of the invention, the biologically active agent comprises a cell.

In some embodiments of the invention, the biologically active component comprises chitosan.

In some embodiments, the ECM material and, hence ECM encasement structures formed therefrom include at least one pharmacological agent or composition (or drug), i.e. an agent or composition that is capable of producing a desired biological effect in vivo, e.g., stimulation or suppression of apoptosis, stimulation or suppression of an immune response, etc.

In some embodiments, the pharmacological agent or composition is selected from the group comprising antibiotics or antifungal agents, anti-viral agents, anti-pain agents, anesthetics, analgesics, steroidal anti-inflammatories, non-steroidal anti-inflammatories, anti-neoplastics, anti-spasmodics, modulators of cell-extracellular matrix interactions, proteins, hormones, enzymes and enzyme inhibitors, anticoagulants and/or antithrombic agents, DNA, RNA, modified DNA and RNA, NSAIDs, inhibitors of DNA, RNA or protein synthesis, polypeptides, oligonucleotides, polynucleotides, nucleoproteins, compounds modulating cell migration, compounds modulating proliferation and growth of tissue, and vasodilating agents.

In some embodiments of the invention, the pharmacological agent specifically comprises an anti-inflammatory agent or composition.

In some embodiments of the invention, the pharmacological agent comprises a statin, i.e. a HMG-CoA reductase inhibitor.

According to the invention, upon deployment of an encased medical device of the invention, i.e. an ECM encasement structure having a medical device therein or a medical device (or instrument) coated with an ECM composition of the invention, modulated healing and regeneration of tissue structures with site-specific structural and functional properties are effectuated.

BRIEF DESCRIPTION OF THE DRAWINGS

Further features and advantages will become apparent from the following and more particular description of the preferred embodiments of the invention, as illustrated in the accompanying drawings, and in which like referenced characters generally refer to the same parts or elements throughout the views, and in which.

DETAILED DESCRIPTION OF THE PREFERRED EMBODIMENT

Figure 1:
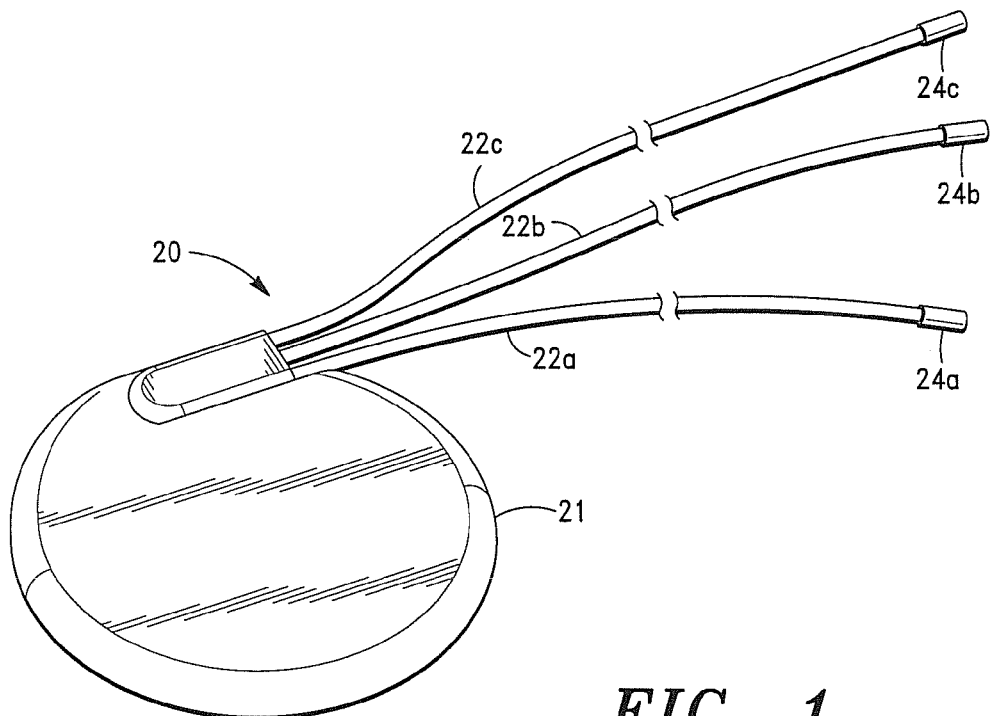
FIG. 1 is a perspective view of a biventricular (Bi-V) pacemaker.

Before describing the present invention in detail, it is to be understood that this invention is not limited to particularly exemplified apparatus, systems, structures or methods as such may, of course, vary. Thus, although a number of apparatus, systems and methods similar or equivalent to those described herein can be used in the practice of the present invention, the preferred apparatus, systems, structures and methods are described herein.

It is also to be understood that, although the present invention is described and illustrated in connection with encased medical devices, the invention is not limited to medical devices. According to the invention, the extracellular matrix (ECM) structures and compositions of the invention can also be employed to encase other devices, including, by way of example, a tracking device.

It is also to be understood that the terminology used herein is for the purpose of describing particular embodiments of the invention only and is not intended to be limiting.

Unless defined otherwise, all technical and scientific terms used herein have the same meaning as commonly understood by one having ordinary skill in the art to which the invention pertains.

Further, all publications, patents and patent applications cited herein, whether supra or infra, are hereby incorporated by reference in their entirety.

As used in this specification and the appended claims, the singular forms "a, "an" and "the" include plural referents unless the content clearly dictates otherwise. Thus, for example, reference to "an active" includes two or more such actives and the like.

Further, ranges can be expressed herein as from "about" or "approximately" one particular value, and/or to "about" or "approximately" another particular value. When such a range is expressed, another embodiment includes from the one particular value and/or to the other particular value. Similarly, when values are expressed as approximations, by use of the antecedent "about" or "approximately", it will be understood that the particular value forms another embodiment. It will be further understood that the endpoints of each of the ranges are significant both in relation to the other endpoint, and independently of the other endpoint.

It is also understood that there are a number of values disclosed herein, and that each value is also herein disclosed as "about" or "approximately" that particular value in addition to the value itself. For example, if the value "10" is disclosed, then "approximately 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed then "less than or equal to 10" as well as "greater than or equal to 10" is also disclosed.

DEFINITIONS

The term "medical device", as used herein, means and includes any device configured for insertion or implantation in the body of a warm blooded mammal, including humans and primates; avians; domestic household or farm animals, such as cats, dogs, sheep, goats, cattle, horses and pigs; laboratory animals, such as mice, rats and guinea pigs; fish; reptiles; zoo and wild animals; and the like. The term "medical device" thus includes, without limitation, a pacemaker, defibrillator, synthetic heart valve, ventricular assist device, artificial heart, physiological sensor, catheter, and associated components thereof, including electrical leads and lines associated therewith.

The terms "extracellular matrix", "ECM" and "ECM material" are used interchangeably herein, and mean and include a collagen-rich substance that is found in between cells in mammalian tissue, and any material processed therefrom, e.g. decellularized ECM. According to the invention, the ECM material can be derived from a variety of mammalian tissue sources, including, without limitation, small intestine submucosa (SIS), urinary bladder submucosa (UBS), stomach submucosa (SS), central nervous system tissue, epithelium of mesodermal origin, i.e. mesothelial tissue, dermal extracellular matrix, subcutaneous extracellular matrix, gastrointestinal extracellular matrix, i.e. large and small intestines, tissue surrounding growing bone, placental extracellular matrix, ornamentum extracellular matrix, cardiac extracellular matrix, e.g., pericardium and/or myocardium, kidney extracellular matrix, pancreas extracellular matrix, lung extracellular matrix, and combinations thereof. The ECM material can also comprise collagen from mammalian sources.

The terms "urinary bladder submucosa (UBS)", "small intestine submucosa (SIS)" and "stomach submucosa (SS)" also mean and include any UBS and/or SIS and/or SS material that includes the tunica mucosa (which includes the transitional epithelial layer and the tunica propria), submucosal layer, one or more layers of muscularis, and adventitia (a loose connective tissue layer) associated therewith.

The ECM material can also be derived from basement membrane of mammalian tissue/organs, including, without limitation, urinary basement membrane (UBM), liver basement membrane (LBM), and amnion, chorion, allograft pericardium, allograft acellular dermis, amniotic membrane, Wharton's jelly, and combinations thereof.

Additional sources of mammalian basement membrane include, without limitation, spleen, lymph nodes, salivary glands, prostate, pancreas and other secreting glands.

The ECM material can also be derived from other sources, including, without limitation, collagen from plant sources and synthesized extracellular matrices, i.e. cell cultures.

The term "angiogenesis", as used herein, means a physiologic process involving the growth of new blood vessels from pre-existing blood vessels.

The term "neovascularization", as used herein, means and includes the formation of functional vascular networks that can be perfused by blood or blood components. Neovascularization includes angiogenesis, budding angiogenesis, intussuceptive angiogenesis, sprouting angiogenesis, therapeutic angiogenesis and vasculogenesis.

The terms "biologically active agent" and "biologically active composition" are used interchangeably herein, and mean and include agent that induces or modulates a physiological or biological process, or cellular activity, e.g., induces proliferation, and/or growth and/or regeneration of tissue.

The terms "biologically active agent" and "biologically active composition" thus mean and include, without limitation, the following growth factors: platelet derived growth factor (PDGF), epidermal growth factor (EGF), transforming growth factor alpha (TGF-alpha), transforming growth factor beta (TGF-beta), fibroblast growth factor-2 (FGF-2), basic fibroblast growth factor (bFGF), vascular epithelial growth factor (VEGF), hepatocyte growth factor (HGF), insulin-like growth factor (IGF), nerve growth factor (NGF), platlet derived growth factor (PDGF), tumor necrosis factor alpha (TNA-alpha), and placental growth factor (PLGF).

The terms "biologically active agent" and "biologically active composition" also mean and include, without limitation, human embryonic stem cells, fetal cardiomyocytes, myofibroblasts, mesenchymal stem cells, autotransplated expanded cardiomyocytes, adipocytes, totipotent cells, pluripotent cells, blood stem cells, myoblasts, adult stem cells, bone marrow cells, mesenchymal cells, embryonic stem cells, parenchymal cells, epithelial cells, endothelial cells, mesothelial cells, fibroblasts, osteoblasts, chondrocytes, exogenous cells, endogenous cells, stem cells, hematopoietic stem cells, bone-marrow derived progenitor cells, myocardial cells, skeletal cells, fetal cells, undifferentiated cells, multipotent progenitor cells, unipotent progenitor cells, monocytes, cardiac myoblasts, skeletal myoblasts, macrophages, capillary endothelial cells, xenogenic cells, allogenic cells, and post-natal stem cells.

The terms "biologically active agent" and "biologically active composition" also mean and include, without limitation, the following biologically active agents (referred to interchangeably herein as a "protein", "peptide" and "polypeptide"): collagen (types I-V), proteoglycans, glycosaminoglycans (GAGs), glycoproteins, growth factors, cytokines, cell-surface associated proteins, cell adhesion molecules (CAM), angiogenic growth factors, endothelial ligands, matrikines, cadherins, immuoglobins, fibril collagens, non-fibrallar collagens, basement membrane collagens, multiplexins, small-leucine rich proteoglycans, decorins, biglycans, fibromodulins, keratocans, lumicans, epiphycans, heparin sulfate proteoglycans, perlecans, agrins, testicans, syndecans, glypicans, serglycins, selectins, lecticans, aggrecans, versicans, neurocans, brevicans, cytoplasmic domain-44 (CD-44), macrophage stimulating factors, amyloid precursor proteins, heparins, chondroitin sulfate B (dermatan sulfate), chondroitin sulfate A, heparin sulfates, hyaluronic acids, fibronectins, tenascins, elastins, fibrillins, laminins, nidogen/enactins, fibulin I, finulin II, integrins, transmembrane molecules, thrombospondins, ostepontins, and angiotensin converting enzymes (ACE).

The terms "pharmacological agent", "active agent", "drug" and "active agent formulation" are used interchangeably herein, and mean and include an agent, drug, compound, composition of matter or mixture thereof, including its formulation, which provides some therapeutic, often beneficial, effect. This includes any physiologically or pharmacologically active substance that produces a localized or systemic effect or effects in animals, including warm blooded mammals, humans and primates; avians; domestic household or farm animals, such as cats, dogs, sheep, goats, cattle, horses and pigs; laboratory animals, such as mice, rats and guinea pigs; fish; reptiles; zoo and wild animals; and the like.

The terms "pharmacological agent", "active agent", "drug" and "active agent formulation" thus mean and include, without limitation, antibiotics, anti-arrhythmic agents, antiviral agents, analgesics, steroidal anti-inflammatories, non-steroidal anti-inflammatories, anti-neoplastics, anti-spasmodics, modulators of cell-extracellular matrix interactions, proteins, hormones, growth factors, matrix metalloproteinases (MMPS), enzymes and enzyme inhibitors, anticoagulants and/or antithrombic agents, DNA, RNA, modified DNA and RNA, NSAIDs, inhibitors of DNA, RNA or protein synthesis, polypeptides, oligonucleotides, polynucleotides, nucleoproteins, compounds modulating cell migration, compounds modulating proliferation and growth of tissue, and vasodilating agents.

The terms "pharmacological agent", "active agent", "drug" and "active agent formulation" thus include, without limitation, atropine, tropicamide, dexamethasone, dexamethasone phosphate, betamethasone, betamethasone phosphate, prednisolone, triamcinolone, triamcinolone acetonide, fluocinolone acetonide, anecortave acetate, budesonide, cyclosporine, FK-506, rapamycin, ruboxistaurin, midostaurin, flurbiprofen, suprofen, ketoprofen, diclofenac, ketorolac, nepafenac, lidocaine, neomycin, polymyxin b, bacitracin, gramicidin, gentamicin, oyxtetracycline, ciprofloxacin, ofloxacin, tobramycin, amikacin, vancomycin, cefazolin, ticarcillin, chloramphenicol, miconazole, itraconazole, trifluridine, vidarabine, ganciclovir, acyclovir, cidofovir, ara-amp, foscarnet, idoxuridine, adefovir dipivoxil, methotrexate, carboplatin, phenylephrine, epinephrine, dipivefrin, timolol, 6-hydroxydopamine, betaxolol, pilocarpine, carbachol, physostigmine, demecarium, dorzolamide, brinzolamide, latanoprost, sodium hyaluronate, insulin, verteporfin, pegaptanib, ranibizumab, and other antibodies, antineoplastics, anti VGEFs, ciliary neurotrophic factor, brain-derived neurotrophic factor, bFGF, Caspase-1 inhibitors, Caspase-3 inhibitors, α-Adrenoceptors agonists, NMDA antagonists, Glial cell line-derived neurotrophic factors (GDNF), pigment epithelium-derived factor (PEDF), and NT-3, NT-4, NGF, IGF-2.

The terms "pharmacological agent", "active agent", "drug" and "active agent formulation" further mean and include the following Class I-Class V antiarrhythmic agents: (Class Ia) quinidine, procainamide and disopyramide; (Class Ib) lidocaine, phenytoin and mexiletine; (Class Ic) flecainide, propafenone and moricizine; (Class II) propranolol, esmolol, timolol, metoprolol and atenolol; (Class III) amiodarone, sotalol, ibutilide and dofetilide; (Class IV) verapamil and diltiazem) and (Class V) adenosine and digoxin.

The terms "pharmacological agent", "active agent", "drug" and "active agent formulation" further mean and include, without limitation, the following antiobiotics: aminoglycosides, cephalosporins, chloramphenicol, clindamycin, erythromycins, fluoroquinolones, macrolides, azolides, metronidazole, penicillins, tetracyclines, trimethoprim-sulfamethoxazole and vancomycin.

The terms "pharmacological agent", "active agent", "drug" and "active agent formulation" further include, without limitation, the following steroids: andranes (e.g., testosterone), cholestanes, cholic acids, corticosteroids (e.g., dexamethasone), estraenes (e.g., estradiol) and pregnanes (e.g., progesterone).

The terms "pharmacological agent", "active agent", "drug" and "active agent formulation" can further include one or more classes of narcotic analgesics, including, without limitation, morphine, codeine, heroin, hydromorphone, levorphanol, meperidine, methadone, oxycodone, propoxyphene, fentanyl, methadone, naloxone, buprenorphine, butorphanol, nalbuphine and pentazocine.

The terms "pharmacological agent", "active agent", "drug" and "active agent formulation" can further include one or more classes of topical or local anesthetics, including, without limitation, esters, such as benzocaine, chloroprocaine, cocaine, cyclomethycaine, dimethocaine/larocaine, piperocaine, propoxycaine, procaine/novacaine, proparacaine, and tetracaine/amethocaine. Local anesthetics can also include, without limitation, amides, such as articaine, bupivacaine, cinchocaine/dibucaine, etidocaine, levobupivacaine, lidocaine/lignocaine, mepivacaine, prilocaine, ropivacaine, and trimecaine. Local anesthetics can further include combinations of the above from either amides or esters.

The terms "pharmacological agent", "active agent", "drug" and "active agent formulation" can further include one or more classes of cytotoxic anti-neoplastic agents or chemotherapy agents, including, without limitation, alkylating agents, cisplatin, carboplatin, oxaliplatin, mechlorethamine, cyclophosphamide, chlorambucil, and ifosfamide.

Chemotherapy agents can also include, without limitation, antimetabolites, such as purine analogues, pyrimidine analogues and antifolates, plant alkaloids, such as vincristine, vinblastine, vinorelbine, vindesine, podophyllotoxin, etoposide and teniposide, taxanes, such as paclitaxel and docetaxel, topoisomerase inhibitors, such as irinotecan, topotecan, amsacrine, etoposide, etoposide phosphate and teniposide, cytotoxic antibiotics, such as actinomyocin, bleomycin, plicamycin, mytomycin and anthracyclines, such as doxorubicin, daunorubicin, valrubicin, idarubicin, epirubicin, and antibody treatments, such as abciximab, adamlimumab, alamtuzumab, basiliximab, belimumab, bevacizumab, brentuximab vedotin, canakinumab, cetuximab, certolizumab pego, daclizumab, denosumab, eculizumab, efalizumab, gemtuzumab, golimumab, ibritumomab tiuxetan, infliximab, ipilimumab, muromonab-CD3, natalizumab, ofatumumab, omalizumab, palivizumab, panitumumab, ranibizumab, rituximab, tocilizumab (atlizumab), tositumomab and trastuzumab.

The terms "anti-inflammatory" and "anti-inflammatory agent" are also used interchangeably herein, and mean and include a "pharmacological agent" and/or "active agent formulation", which, when a therapeutically effective amount is administered to a subject, prevents or treats bodily tissue inflammation i.e. the protective tissue response to injury or destruction of tissues, which serves to destroy, dilute, or wall off both the injurious agent and the injured tissues.

Anti-inflammatory agents thus include, without limitation, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol propionate, clobetasone butyrate, clopirac, cloticasone propionate, connethasone acetate, cortodoxone, decanoate, deflazacort, delatestryl, depo-testosterone, desonide, desoximetasone, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, mesterolone, methandrostenolone, methenolone, methenolone acetate, methylprednisolone suleptanate, momiflumate, nabumetone, nandrolone, naproxen, naproxen sodium, naproxol, nimazone, olsalazine sodium, orgotein, orpanoxin, oxandrolane, oxaprozin, oxyphenbutazone, oxymetholone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, stanozolol, sudoxicam, sulindac, suprofen, talmetacin, talniflumate, talosalate, tebufelone, tenidap, tenidap sodium, tenoxicam, tesicam, tesimide, testosterone, testosterone blends, tetrydamine, tiopinac, tixocortol pivalate, tolmetin, tolmetin sodium, triclonide, triflumidate, zidometacin, and zomepirac sodium.

The term "pharmacological composition", as used herein, means and includes a composition comprising a "pharmacological agent" and/or a "biologically active agent" and/or any additional agent or component identified herein.

The term "therapeutically effective", as used herein, means that the amount of the "pharmacological composition" and/or "pharmacological agent" and/or "biologically active agent" administered is of sufficient quantity to ameliorate one or more causes, symptoms, or sequelae of a disease or disorder. Such amelioration only requires a reduction or alteration, not necessarily elimination, of the cause, symptom, or sequelae of a disease or disorder.

The terms "prevent" and "preventing" are used interchangeably herein, and mean and include reducing the frequency or severity of a disease or condition. The term does not require an absolute preclusion of the disease or condition. Rather, this term includes decreasing the chance for disease occurrence.

The terms "treat" and "treatment" are used interchangeably herein, and mean and include medical management of a patient with the intent to cure, ameliorate, stabilize, or prevent a disease, pathological condition, or disorder. The terms include "active treatment", i.e. treatment directed specifically toward the improvement of a disease, pathological condition, or disorder, and "causal treatment", i.e. treatment directed toward removal of the cause of the associated disease, pathological condition, or disorder.

The terms "treat" and "treatment" further include "palliative treatment", i.e. treatment designed for the relief of symptoms rather than the curing of the disease, pathological condition, or disorder, "preventative treatment", i.e. treatment directed to minimizing or partially or completely inhibiting the development of the associated disease, pathological condition, or disorder, and "supportive treatment", i.e. treatment employed to supplement another specific therapy directed toward the improvement of the associated disease, pathological condition, or disorder.

The terms "patient" and "subject" are used interchangeably herein, and mean and include warm blooded mammals, humans and primates; avians; domestic household or farm animals, such as cats, dogs, sheep, goats, cattle, horses and pigs; laboratory animals, such as mice, rats and guinea pigs; fish; reptiles; zoo and wild animals; and the like.

The term "comprise" and variations of the term, such as "comprising" and "comprises," means "including, but not limited to" and is not intended to exclude, for example, other additives, components, integers or steps.

The following disclosure is provided to further explain in an enabling fashion the best modes of performing one or more embodiments of the present invention. The disclosure is further offered to enhance an understanding and appreciation for the inventive principles and advantages thereof, rather than to limit in any manner the invention. The invention is defined solely by the appended claims, including any amendments made during the pendency of this application, and all equivalents of those claims as issued.

As stated above, it is understood that, although the present invention is described and illustrated in connection with encased medical devices, the invention is not limited to medical devices. According to the invention, the extracellular matrix (ECM) structures and compositions of the invention can also be employed to encase other devices, including, by way of example, a tracking device.

It is also understood that, although the present invention is described and illustrated in connection with a pacemaker, the invention is not limited to the noted medical device. Indeed, as stated above, the ECM encasement structures and compositions of the invention can also be employed to encase other medical devices, including without limitation, a defibrillator, synthetic heart valve, ventricular assist device, artificial heart, physiological sensor, catheter, and associated components thereof, including electrical leads and lines associated therewith.

As discussed above, in one embodiment, the present invention is directed to extracellular matrix (ECM) encasement structures and compositions for encasing medical devices.

In another embodiment of the invention, there is provided a medical device (or instrument) that includes at least one coating of an ECM composition; the ECM composition similarly including at least one ECM material.

According to the invention, upon deployment of an ECM encasement structure having a medical device therein or a medical device (or instrument) coated with an ECM composition of the invention, modulated healing and regeneration of tissue structures with site-specific structural and functional properties are effectuated.

The phrase "modulated healing", as used herein, and variants of this language generally refer to the modulation (e.g., alteration, delay, retardation, reduction, etc.) of a process involving different cascades or sequences of naturally occurring tissue repair in response to localized tissue damage or injury, substantially reducing their inflammatory effect. Modulated healing, as used herein, includes many different biologic processes, including epithelial growth, fibrin deposition, platelet activation and attachment, inhibition, proliferation and/or differentiation, connective fibrous tissue production and function, angiogenesis, and several stages of acute and/or chronic inflammation, and their interplay with each other.

For example, in some embodiments, the ECM compositions of the invention are specifically formulated (or designed) to alter, delay, retard, reduce, and/or detain one or more of the phases associated with healing of damaged tissue, including, but not limited to, the inflammatory phase (e.g., platelet or fibrin deposition), and the proliferative phase.

In some embodiments, "modulated healing" refers to the ability of an ECM composition to alter a substantial inflammatory phase (e.g., platelet or fibrin deposition) at the beginning of the tissue healing process. As used herein, the phrase "alter a substantial inflammatory phase" refers to the ability of an ECM composition to substantially reduce the inflammatory response at an injury site.

In such an instance, a minor amount of inflammation may ensue in response to tissue injury, but this level of inflammation response, e.g., platelet and/or fibrin deposition, is substantially reduced when compared to inflammation that takes place in the absence of an ECM composition of the invention.

For example, the ECM compositions discussed herein have been shown experimentally to delay or alter the inflammatory response associated with damaged tissue, as well as excessive formation of connective fibrous tissue following tissue damage or injury. The ECM compositions have also been shown experimentally to delay or reduce fibrin deposition and platelet attachment to a blood contact surface following tissue damage.

In some embodiments of the invention, "modulated healing" refers to the ability of an ECM composition of the invention to induce host tissue proliferation, bioremodeling, including neovascularization, e.g., vasculogenesis, angiogenesis, and intussusception, and regeneration of tissue structures with site-specific structural and functional properties.

Accordingly, the ECM compositions discussed herein provide an excellent bioabsorbable cellular interface suitable for use with a medical device or surgical instrument.

As indicated above, in one embodiment of the invention, the ECM encasement structures comprise an ECM based pocket or pouch that is configured to receive a medical device therein.

According to the invention, the encased medical device and associated components can comprise, without limitation, a pacemaker, defibrillator, synthetic heart valve, ventricular assist device, artificial heart, physiological sensor, catheter, and the electrical leads and lines associated therewith.

According to the invention, the entire medical device or a portion thereof can be encased in the ECM encasement structure. Thus, in some embodiments of the invention, the medical device housing and a portion of the device leads are encased in an ECM based pouch. In the noted embodiments, the device leads can also be coated with an ECM composition of the invention.

In some embodiments of the invention, the ECM encasement structure includes at least one lead conduit, more preferably, a plurality of lead conduits that are configured to encase the medical device leads.

In a preferred embodiment, the ECM encasement structure comprises (or is constructed of) an ECM composition that includes at least one ECM material (hereinafter "ECM pouch"). According to the invention, the ECM pouch can comprise various shapes and sizes to accommodate virtually all shapes and sizes of medical devices.

As also indicated above, in other embodiments of the invention, there are provided medical devices that include at least one coating of an ECM composition; the ECM composition similarly including at least one ECM material. According to the invention, the medical devices can similarly include, without limitation, the aforementioned devices and associated components, as well as surgical instruments.

According to the invention, the ECM material can be derived from various mammalian tissue sources and methods for preparing same, such as disclosed in U.S. Pat. Nos. 7,550,004, 7,244,444, 6,379,710, 6,358,284, 6,206,931, 5,733,337 and 4,902,508 and U.S. application Ser. No. 12/707,427; which are incorporated by reference herein in their entirety.

The ECM material can also be sterilized via applicant's proprietary sterilization (i.e. novasterillis) process, as disclosed in Co-Pending U.S. application Ser. No. 13/480,205; which is expressly incorporated herein in their entirety.

In a preferred embodiment, the mammalian tissue sources include, without limitation, small intestine submucosa (SIS), urinary bladder submucosa (UBS), stomach submucosa (SS), central nervous system tissue, epithelium of mesodermal origin, i.e. mesothelial tissue, dermal extracellular matrix, subcutaneous extracellular matrix, gastrointestinal extracellular matrix, i.e. large and small intestines, tissue surrounding growing bone, placental extracellular matrix, ornamentum extracellular matrix, cardiac extracellular matrix, e.g., pericardium and/or myocardium, kidney extracellular matrix, pancreas extracellular matrix, lung extracellular matrix, and combinations thereof. The ECM material can also comprise collagen from mammalian sources.

The ECM material can also be derived from the same or different mammalian tissue sources, as disclosed in Co-Pending application Ser. Nos. 13/033,053 and 13/033,102; which are incorporated by reference herein.

As stated above, in some embodiments of the invention, the ECM material and, hence, ECM encasement structures formed therefrom include at least one additional biologically active agent or composition, i.e. an agent that induces or modulates a physiological or biological process, or cellular activity, e.g., induces proliferation, and/or growth and/or regeneration of tissue.

Suitable biologically active agents include any of the aforementioned biologically active agents, including, without limitation, the aforementioned cells, proteins and growth factors.

In some embodiments, the ECM material and, hence, ECM encasement structures formed therefrom include at least one pharmacological agent or composition (or drug), i.e. an agent or composition that is capable of producing a desired biological effect in vivo, e.g., stimulation or suppression of apoptosis, stimulation or suppression of an immune response, etc.

Suitable pharmacological agents and compositions include any of the aforementioned agents, including, without limitation, antibiotics, anti-viral agents, analgesics, steroidal anti-inflammatories, non-steroidal anti-inflammatories, anti-neoplastics, anti-spasmodics, modulators of cell-extracellular matrix interactions, proteins, hormones, enzymes and enzyme inhibitors, anticoagulants and/or antithrombic agents, DNA, RNA, modified DNA and RNA, NSAIDs, inhibitors of DNA, RNA or protein synthesis, polypeptides, oligonucleotides, polynucleotides, nucleoproteins, compounds modulating cell migration, compounds modulating proliferation and growth of tissue, and vasodilating agents.

In some embodiments of the invention, the pharmacological agent comprises an anti-inflammatory agent.

In some embodiments of the invention, the pharmacological agent comprises a statin, i.e. a HMG-CoA reductase inhibitor. According to the invention, suitable statins include, without limitation, atorvastatin (Lipitor®), cerivastatin, fluvastatin (Lescol®), lovastatin (Mevacor®, Altocor®, Altoprev®), mevastatin, pitavastatin (Livalo®, Pitava®), pravastatin (Pravachol®, Selektine®, Lipostat®), rosuvastatin (Crestor®), and simvastatin (Zocor®, Lipex®). Several actives comprising a combination of a statin and another agent, such as ezetimbe/simvastatin (Vytorin®), are also suitable.

Applicant has found that the noted statins exhibit numerous beneficial properties that provide several beneficial biochemical actions or activities. The properties and beneficial actions are set forth in Applicant's Co-Pending application Ser. No. 13/373,569, filed on Sep. 24, 2012 and Ser. No. 13/782,024, filed on Mar. 1, 2013; which are incorporated by reference herein in their entirety.

In some embodiments of the invention, the pharmacological agent comprises chitosan. As also set forth in detail in Co-Pending application Ser. No. 13/573,569, chitosan also exhibits numerous beneficial properties that provide several beneficial biochemical actions or activities.

Additional suitable pharmacological agents and compositions that can be delivered within the scope of the invention are disclosed in Pat. Pub. Nos. 20070014874, 20070014873, 20070014872, 20070014871, 20070014870, 20070014869, and 20070014868; which are expressly incorporated by reference herein in its entirety.

According to the invention, the amount of a pharmacological agent added to an ECM composition of the invention will, of course, vary from agent to agent. For example, in one embodiment, wherein the pharmacological agent comprises dicloflenac (Voltaren®), the amount of dicloflenac included in the ECM composition is preferably in the range of 10 μg-75 mg.

According to the invention, the biologically active and pharmacological agents referenced above can comprise any form. In some embodiments of the invention, the biologically active and pharmacological agents, e.g. simvastatin and/or chitosan, comprise microcapsules that provide delayed delivery of the agent contained therein.

As indicated above, upon deployment of an ECM encasement structure or a medical device (or instrument) coated with an ECM composition of the invention, modulated healing and regeneration of tissue structures with site-specific structural and functional properties is effectuated.

Referring now to FIG. 1, there is shown an exemplar implantable medical device; in this instance, a bi-ventricular (Bi-V) pacemaker 20, that can be encased by an ECM encasement structure of the invention. As is well known in the art and illustrated in FIG. 1, the Bi-V pacemaker 20 generally includes a pulse generator 21, electrical leads 22a, 22b, 22c and lead tips or electrodes 24a, 24b, 24c.

As is also well known in the art, the Bi-V pacemaker 20 is used to modulate the heart rate of a patient and prevent a life threatening heart dysfunction, e.g. arrhythmia.

The Bi-V pacemaker 20 is typically implanted transvenously in a patient, wherein two (2) electrical leads, i.e. leads 22a, 22b, are placed in a vein and guided to the right atrium and ventricle of the heart. The leads 22a, 22b are then attached to the heart muscle proximate the noted heart structures.

The third pacemaker lead, i.e., lead 22c, is also guided through a vein to the coronary sinus (i.e. a small vein on the back of the heart) and attached to the heart to pace the left ventricle.

Figure 2:
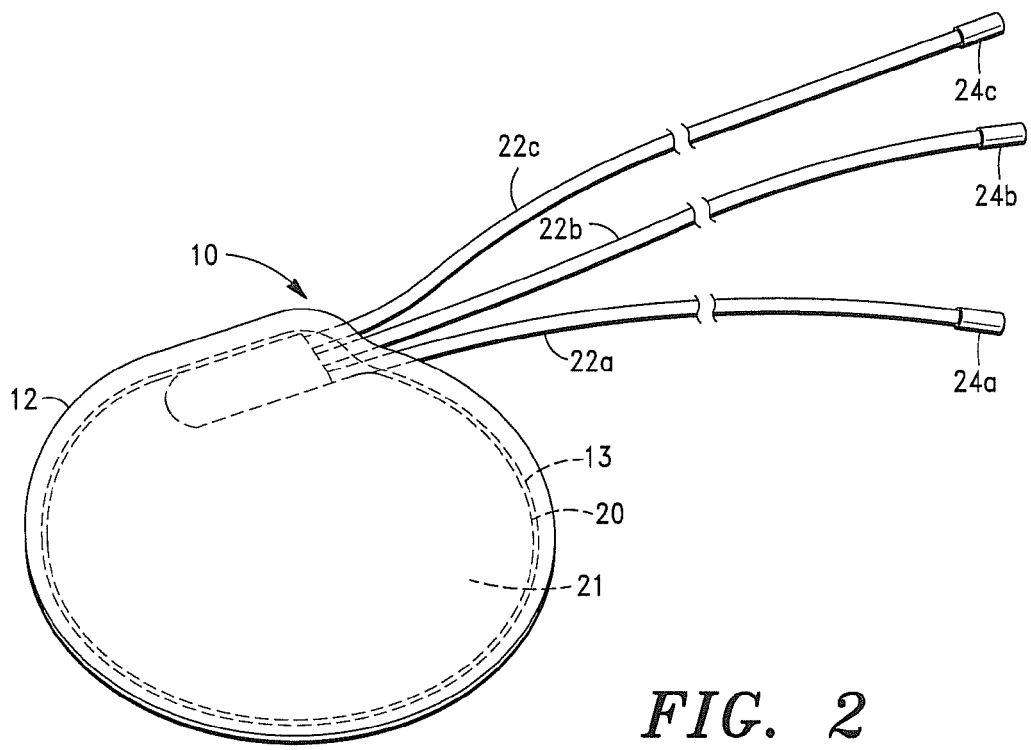
FIG. 2 is a perspective view of one embodiment of an ECM encasement structure having the Bi-V pacemaker shown in FIG. 1 encased therein, in accordance with the invention.

Referring now to FIG. 2, there is shown a first embodiment of an ECM encasement structure of the invention 10, having the medical device 20 encased therein. As illustrated in FIG. 2, in this embodiment, the ECM encasement structure 10 is configured to encase the entire pacemaker 20 and a portion of the leads 22a, 22b, 22c, associated therewith.

The ECM encasement structure 10 generally comprises a pocket or pouch 12 having a cavity therein 13. The cavity 13 is sized and configured to receive and contain a medical device 20 therein.

In a preferred embodiment of the invention, the pouch 12 comprises at least one layer or sheet of encasement material constructed of an ECM composition of the invention. According to the invention, the pouch 12 can also include more than one layer of encasement material, e.g. two (2), three (3) encasement layers, etc. The encasement layers can also comprise the same material, i.e. ECM material or composition, or different materials or compositions.

In some embodiments of the invention, the ECM composition (or encasement layer(s)) and, hence, ECM encasement structure 10 formed therefrom include at least one additional biologically active agent or composition, i.e. an agent that induces or modulates a physiological or biological process, or cellular activity, e.g., induces proliferation, and/or growth and/or regeneration of tissue.

Suitable biologically active agents include any of the aforementioned biologically active agents, including, without limitation, the aforementioned cells, proteins and growth factors.

In some embodiments, the ECM composition (or encasement layer(s)) and, hence, ECM encasement structure 10 formed therefrom include at least one pharmacological agent or composition (or drug), i.e. an agent or composition that is capable of producing a desired biological effect in vivo, e.g., stimulation or suppression of apoptosis, stimulation or suppression of an immune response, etc.

Suitable pharmacological agents and compositions include any of the aforementioned agents, including, without limitation, antibiotics, anti-viral agents, analgesics, and steroidal and non-steroidal anti-inflammatories.

According to the invention, the biologically active and pharmacological agents can be incorporated into the ECM composition (and/or material) and/or deposited on the outer surface of an outer encasement layer.

Figure 3:
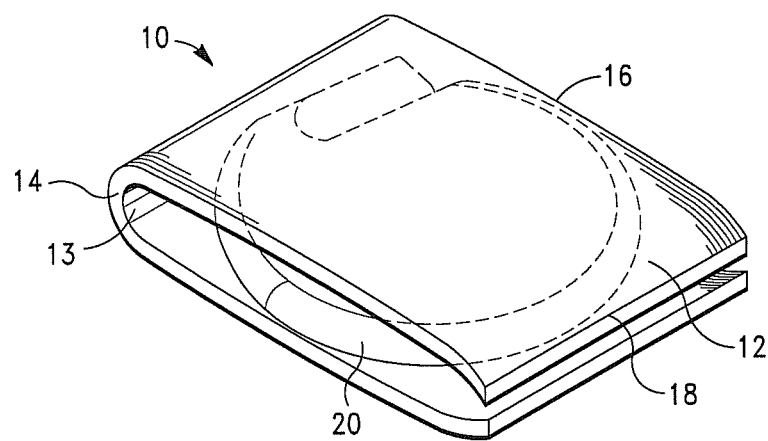
FIG. 3 is a perspective view of an ECM encasement structure, illustrating a folded pre-lamination configuration of an ECM pouch layer, in accordance with the invention.
Figure 4:
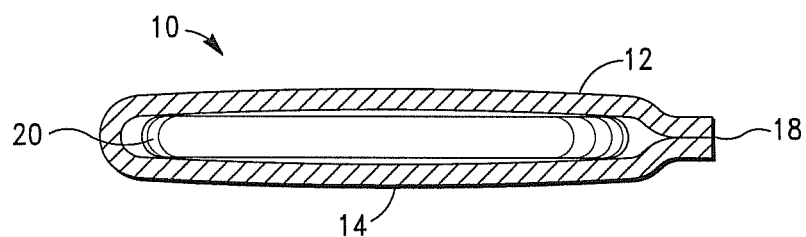
FIG. 4 is a front, partial sectional plan view of the ECM encasement structure shown in FIG. 3, illustrating a laminated ECM pouch layer end, in accordance with the invention.

Referring now to FIG. 3, there is shown a perspective view of the ECM encasement structure 10, showing a folded pre-lamination configuration of the encasement layer (denoted "14"). As illustrated in FIG. 3, in the noted embodiment, the encasement layer 14 comprises a single sheet of encasement material. To form the pouch 12, the encasement layer 14 is folded over and laminated on the end 18 (see FIG. 4) and sides 16.

Figure 5:
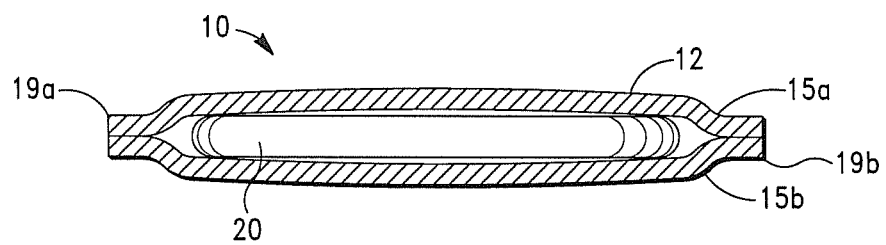
FIG. 5 is a front, partial sectional plan view of another embodiment of an ECM encasement structure, in accordance with the invention.

Referring now to FIG. 5, in some embodiments of the invention, the pouch 12 similarly comprises one encasement layer 14. However, in the noted embodiments, two (2) sheets of encasement material or layers 15a, 15b are employed to form the pouch 12. The layers 15a, 15b are laminated on both ends 19a, 19b, as shown in FIG. 5, and sides.

According to the invention, the sides and ends of encasement layers of the invention can be laminated by various conventional means, such as stitching, including ECM stitches, stapled, adhesives. The encasement layers can also be laminated via microneedles and/or microneedle structures, such as disclosed in Co-Pending application Ser. No. 13,686, 131.

Figure 6:
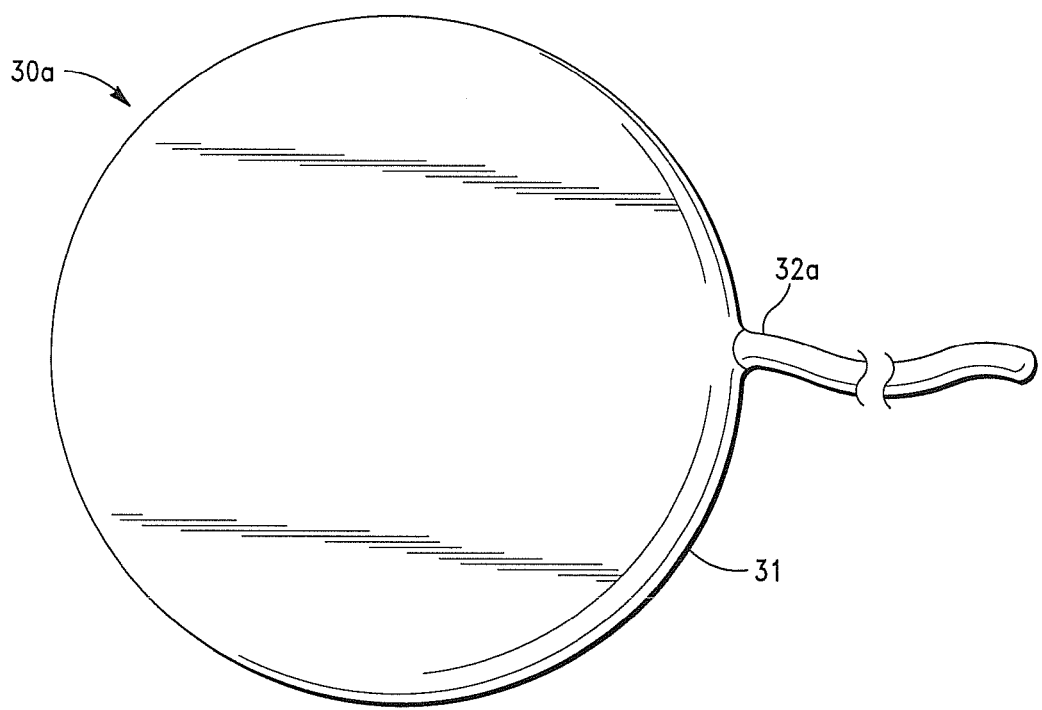
FIGS. 6 and 7 are top plane views of further embodiments of ECM encasement structures, wherein the encasement structures include electrical lead conduits; in accordance with the invention.
Figure 7:
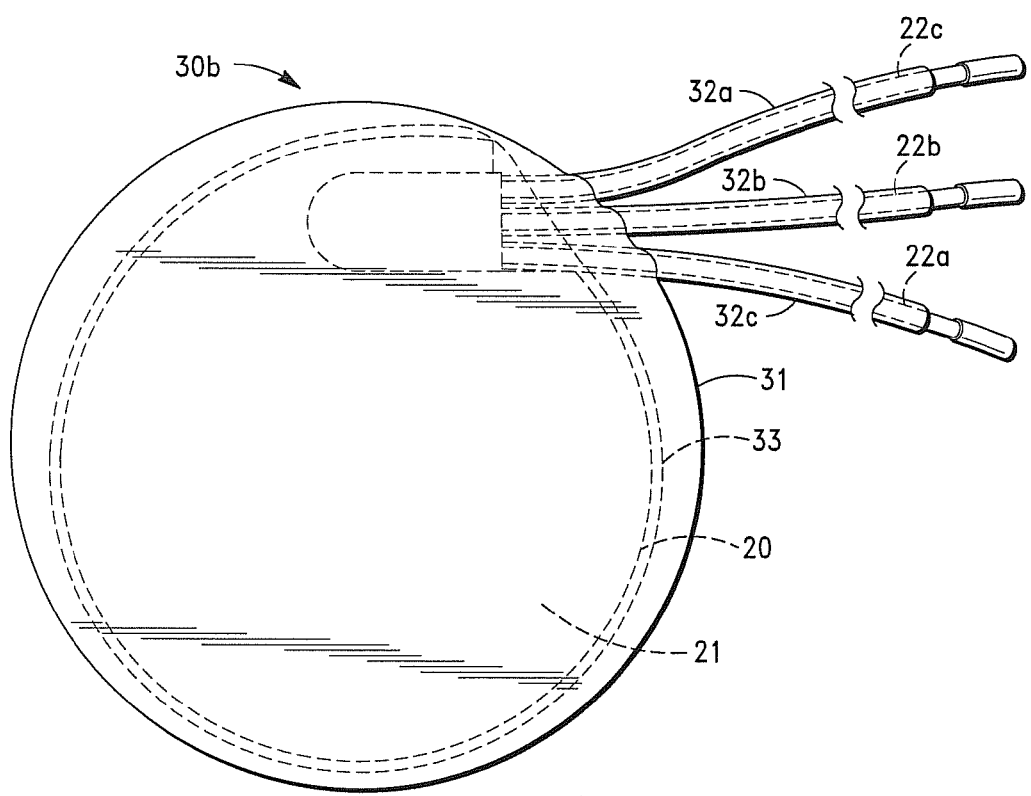

Referring now to FIGS. 6 and 7, there is shown further embodiments of ECM encasement structures of the invention that are configured to encase medical devices, as well as the electrical leads associated therewith. Referring first to FIG. 6, in some embodiments, the ECM encasement structure 30a similarly comprises a pocket or pouch 31 having a cavity therein, such as shown in FIG. 2. The cavity is also sized and configured to receive and contain a medical device therein.

As illustrated in FIG. 6, the ECM encasement structure 30a further includes an integral lead conduit 32a that is configured to receive at least one medical device, e.g. pacemaker, lead therein.

Referring now to FIG. 7 there is shown another embodiment of an ECM encasement structure 30b, which similarly comprises a pocket or pouch 31 having a cavity 33 therein. As illustrated in FIG. 7, the cavity 33 is similarly designed and configured to contain a medical device; in this instance, pacemaker 20, therein.

In this embodiment, the ECM encasement structure 32b includes a plurality of lead conduits 32a, 32b, 32c that are configured to receive a plurality of device electrical leads, in this instance, pacemaker leads 22a, 22b, 22c, therein.

According to the invention, the ECM encasement structures 30a, 30b can comprise any of the aforementioned ECM compositions and/or materials. The ECM compositions and/or materials can similarly include any of the aforementioned biologically active or pharmacological agents.

The lead conduits 32a, 32b, 32c can also be formed from the same ECM composition and/or material or a different ECM composition and/or material.

As indicated above, in other embodiments of the invention, there are provided medical devices that include at least one coating of an ECM composition of the invention. According to the invention, the medical devices can similarly include, without limitation, the aforementioned devices and associated components, as well as surgical instruments.

Figure 8:
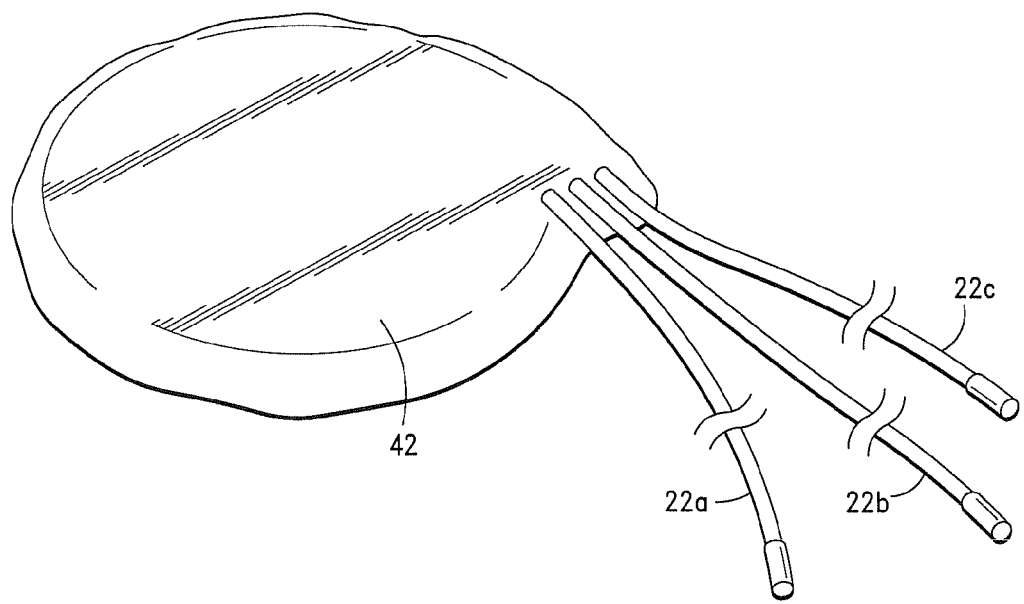
FIG. 8 is a perspective view of one embodiment of a medical device having an ECM composition coating thereon, in accordance with the invention.
Figure 9:
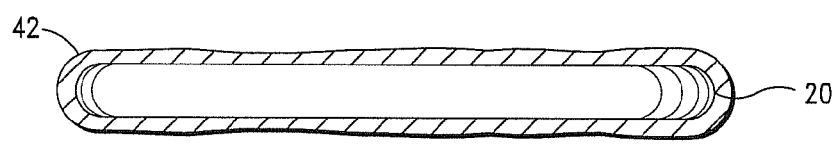
FIG. 9 is a front, partial sectional plan view of the coated medical device shown in FIG. 8, in accordance with the invention.

Referring now to FIGS. 8 and 9, there is shown a medical device, e.g. the Bi-V pacemaker, discussed above, having an ECM composition coating 42 disposed thereon. According to the invention, at least a portion of the medical device is coated with the ECM composition.

In a preferred embodiment, the entire medical device is coated with the ECM coating.

In some embodiments, the entire medical device and electrical leads associated therewith, e.g. leads 22a, 22b, 22c shown in FIG. 6, are coated with the ECM composition.

According to the invention, various conventional means can be employed to form the coated biocompatible and hemocompatible medical device (and associated leads), including spray coating, dipping, etc.

As indicated above, upon deployment of an encased medical device of the invention, i.e. an ECM encasement structure or the coated medical device of the invention, modulated healing and regeneration of tissue structures with site-specific structural and functional properties are effectuated.

As will readily be appreciated by one having ordinary skill in the art, the present invention provides numerous advantages compared to prior art vascular endografts. Among the advantages are the following:

The provision of encasement structures that are configured to encase a medical device therein and that substantially reduce or eliminate the harsh biological responses associated with conventional implanted medical devices, including inflammation, infection and thrombogenesis, when implanted in the body.

The provision of ECM encasement structures that are configured to encase a medical device therein, and effectively improve biological functions and/or promote modulated healing of adjacent tissue and the growth of new tissue when implanted in the body.

The provision of ECM encasement structures that are configured to encase a medical device therein and administer one or more pharmacological or therapeutic agents to a subject when implanted in his/her body.

The provision of medical devices that are configured for insertion or implantation in the body and exhibit enhanced biocompatibility and hemocompatibility when inserted or implanted therein.

Without departing from the spirit and scope of this invention, one of ordinary skill can make various changes and modifications to the invention to adapt it to various usages and conditions. As such, these changes and modifications are properly, equitably, and intended to be, within the full range of equivalence of any subsequently proffered claims.

What is claimed is:

1. An implantable medical device, comprising:
   a coated pacemaker comprising an outer surface having at least one coating comprising an extracellular matrix (ECM) composition disposed thereon, said ECM composition coating forming a sealed ECM encasement structure,
   said ECM composition comprising acellular first ECM from a first mammalian tissue source, said first mammalian tissue source being selected from the group consisting of small intestine submucosa (SIS), urinary bladder submucosa (UBS) and stomach submucosa (SS), said ECM composition further comprising a first bioactive component comprising a statin and a second bioactive component comprising an anti-viral agent, said statin being dispersed within said first ECM,
   said coated pacemaker, when implanted in host tissue of a subject's body, being configured to modulate said subject's heart rate and induce modulated healing, said modulated healing comprising control of inflammation of said host tissue and induced tissue proliferation and bioremodeling of said host tissue.

2. The coated pacemaker of claim 1, wherein said ECM composition further comprises acellular second ECM from a second mammalian tissue source, said second mammalian tissue source being selected from the group consisting of urinary basement membrane (UBM) and liver basement membrane (LBM).

3. The coated pacemaker of claim 1, wherein said ECM composition further comprises a third bioactive component, said third bioactive component comprising a growth factor selected from the group consisting of a platelet derived growth factor (PDGF), epidermal growth factor (EGF), transforming growth factor alpha (TGF-alpha), transforming growth factor beta (TGF-beta), fibroblast growth factor-2 (FGF-2), basic fibroblast growth factor (bFGF), vascular epithelial growth factor (VEGF), hepatocyte growth factor (HGF), insulin-like growth factor (IGF), nerve growth factor (NGF), tumor necrosis factor alpha (TNA-alpha), and placental growth factor (PLGF).

4. The medical device of claim 1, wherein said statin is selected from the group consisting of atorvastatin, cerivastatin, fluvastatin, lovastatin, mevastatin, pitavastatin, pravastatin, rosuvastatin and simvastatin.

\* \* \* \* \*